(12) United States Patent
Crowder et al.

(10) Patent No.: US 8,882,819 B2
(45) Date of Patent: Nov. 11, 2014

(54) HANDHELD DEVICE FOR TREATING ORAL ULCERS AND SORES

(76) Inventors: Richard Crowder, Wichita, KS (US); Adam Crowder, Wichita, KS (US)

( * ) Notice: Subject to any disclaimer, the term of this patent is extended or adjusted under 35 U.S.C. 154(b) by 176 days.

(21) Appl. No.: 13/028,363

(22) Filed: Feb. 16, 2011

(65) Prior Publication Data

US 2012/0207184 A1    Aug. 16, 2012

(51) Int. Cl.
| | |
|---|---|
| *A61N 5/06* | (2006.01) |
| *A61B 18/20* | (2006.01) |
| *A61B 17/00* | (2006.01) |
| *A61B 18/00* | (2006.01) |
| *A61B 19/00* | (2006.01) |

(52) U.S. Cl.
CPC ....... *A61B 18/20* (2013.01); *A61B 2017/00734* (2013.01); *A61B 2018/00452* (2013.01); *A61B 2018/00916* (2013.01); *A61B 2019/521* (2013.01)
USPC .................. 607/89; 606/9; 607/88; 372/38.04

(58) Field of Classification Search
CPC ........... A61B 18/20; A61B 2018/0452; A61B 2018/0916; A61B 2017/0734; A61B 2019/521; H01S 3/10; A61N 5/06
USPC .................................... 607/89, 88; 372/38.04
See application file for complete search history.

(56) References Cited

U.S. PATENT DOCUMENTS

| | | |
|---|---|---|
| 3,163,166 A | 12/1964 | Brant et al. |
| 4,191,750 A | 3/1980 | Hodosh |
| 4,466,956 A | 8/1984 | Leeds |
| 4,702,732 A | 10/1987 | Powers et al. |
| 5,160,316 A | 11/1992 | Henley |
| 5,182,104 A | 1/1993 | Marcus et al. |
| 5,272,716 A * | 12/1993 | Soltz et al. .................... 372/109 |
| 5,279,543 A | 1/1994 | Glikfeld et al. |
| 5,281,218 A | 1/1994 | Imran |
| 5,516,799 A | 5/1996 | Alliger |
| 5,676,648 A | 10/1997 | Henley |
| 5,686,095 A | 11/1997 | Price, Jr. |
| 5,968,005 A | 10/1999 | Tu |
| 6,680,548 B2 * | 1/2004 | Shiue et al. .................... 307/141 |
| 2005/0245998 A1 * | 11/2005 | Pruitt et al. ...................... 607/89 |
| 2006/0030908 A1 * | 2/2006 | Powell et al. .................... 607/88 |
| 2007/0217199 A1 * | 9/2007 | Adam et al. .................. 362/276 |
| 2009/0112296 A1 * | 4/2009 | Weisbart et al. ................ 607/89 |
| 2009/0216219 A1 * | 8/2009 | Venter et al. .................... 606/11 |

\* cited by examiner

*Primary Examiner* — Gary Jackson
*Assistant Examiner* — Boniface N Nganga
(74) *Attorney, Agent, or Firm* — Hovey Williams LLP

(57) ABSTRACT

A device for treating oral ulcers or sores comprises a light source for illuminating a sore or ulcer to be treated; a laser diode for directing laser energy at the sore or ulcer; a regulated power supply for powering the light source and the laser diode at selected power levels; a first switch operable to selectively deliver power from the regulated power supply to the light source; a second switch operable to selectively deliver power from the regulated power supply to the laser diode when the switch is operated by a user to treat the located ulcer or sore; a control device configured to operate the laser diode for a selected time period each time the switch is operated and to then subsequently turn the laser diode off until the switch is operated again; and a portable, handheld housing for housing the laser diode, regulated power supply, switch, and control device.

2 Claims, 2 Drawing Sheets

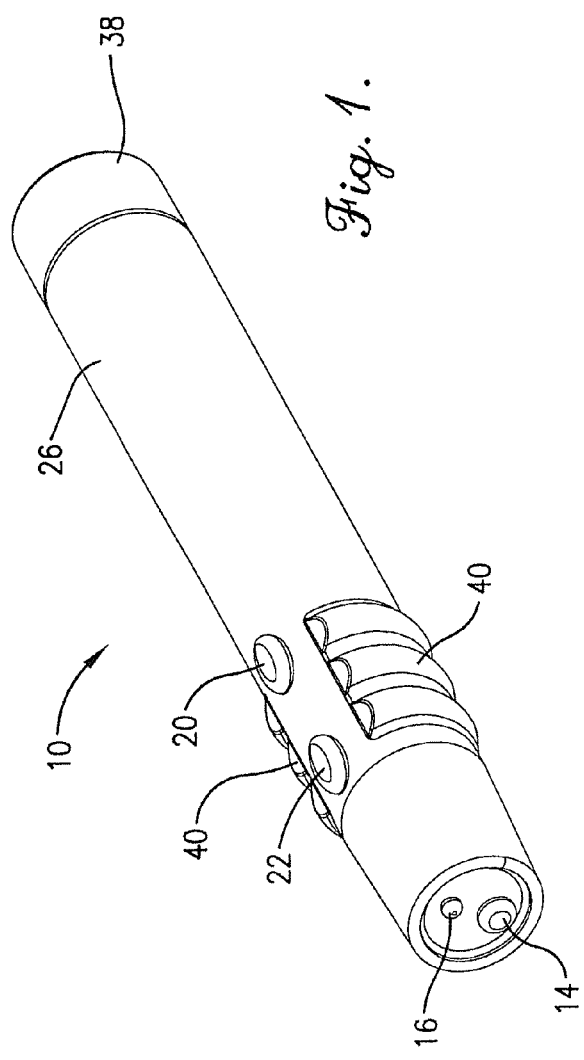
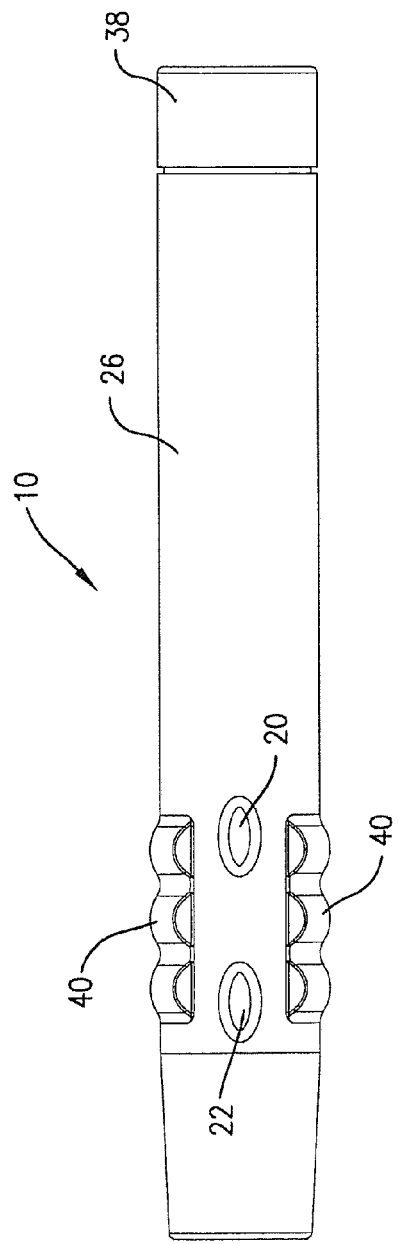

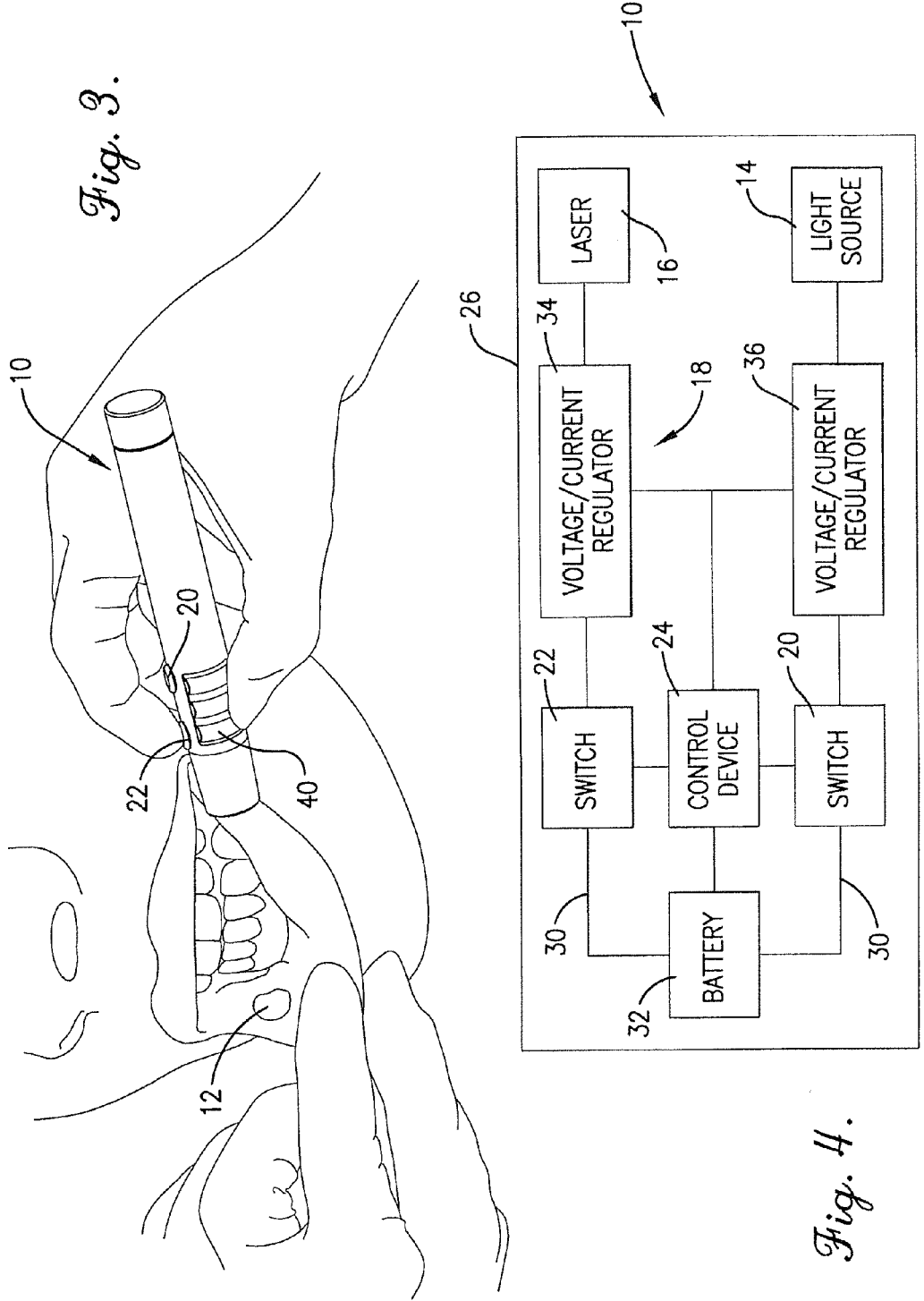

HANDHELD DEVICE FOR TREATING ORAL ULCERS AND SORES

FIELD OF INVENTION

The present invention relates to devices and methods for treating oral ulcers and sores.

BACKGROUND

Canker sores, cold sores, oral warts, fever blisters, acne, gingivitis and other oral ulcers and sores afflict nearly everyone at some point. Such ulcers and sores are caused by a variety of factors and are usually found on the loose tissue of a person's mouth such as the inner cheek, inner lip, tongue, soft palate, or mouth floor.

A number of different treatments can help reduce the pain of these ulcers and sores and speed their healing, including topical compounds, surgery, and laser therapy. Topical compounds such as topical anaesthetics, virucidal agents, nitrate solutions, and anti-inflammatory lotions provide relief to some patients, but their effectiveness is temporary because the compounds quickly wash away in the patients' mouths. Many topical compounds also taste bad and may temporarily discolor a patient's teeth. Surgical procedures are more permanent, but they lead to trauma of the surrounding tissue that is often more painful than the ulcers and sores themselves. Moreover, most patients consider surgery to be too expensive and time-consuming for a medical condition that usually goes away on its own after a few weeks.

Laser therapy is recognized as a safe and effective treatment for oral ulcers and sores. Laser therapy directs radiation of a particular wavelength onto an oral ulcer or sore and has been shown to reduce inflamation by increasing the amount of vaso-dilating and anti-inflammatory compounds in the treated tissue; stimulate increased levels of beta-endorphins that serve as natural analgesics to reduce pain; and speed tissue repair by greatly accelerating the production of ATP (adeno-triphosphate), the chemical energy of cells.

Laser treatment of oral ulcers and sores is typically provided with table-top lasers designed for dentists or surgeons. These devices are large, cumbersome, and expensive, and are thus impractical for everyday treatment of oral ulcers and sores. These devices also must be operated at powered-down levels to avoid unsafe exposure of laser light to the patient and provider.

Some have proposed the use of penlight lasers, laser pointers, and similar inexpensive devices for the treatment of oral sores and ulcers. Unfortunately, these devices often lack sufficient power to induce the above-described bio-stimulatory effects. Also, because of their inexpensive and simple designs, these devices also often operate at inconsistent power levels, do not emit effective and/or consistent wavelengths of laser, and provide no mechanisms to control or monitor the durations of treatment.

SUMMARY

The present invention solves the above-described problems and provides a distinct advance in the art of treatment devices for oral ulcers and sores. More particularly, the invention provides a relatively small, economical, and easy-to-use device that effectively treats oral ulcers and sores via laser therapy.

An embodiment of the device broadly comprises a light source for emitting a beam of visible light; a laser diode for emitting laser energy; a regulated power supply for powering the LED and the laser diode at selected power levels; a first switch operable to selectively deliver power from the regulated power supply to the LED; a second switch operable to selectively deliver power from the regulated power supply to the laser diode; a control device; and a portable, handheld housing for housing the laser diode, regulated power supply, switch, and control device.

The light source is positioned on a distal end of the housing and is provided for illuminating a patient's mouth so that a user may more easily locate a sore or ulcer to treat. In one embodiment, the light source may be a 3.5V light emitting diode (LED) that emits white light.

The laser diode is also positioned on the distal end of the housing and is provided for treating the ulcer or sore once it has been located. In one embodiment, the laser diode may be a 2V red laser diode that emits a spatially coherent, narrow beam of electromagnetic radiation having a wavelength of 600-700 nm.

The regulated power supply controls the power level of the light source and laser diode and may include any circuits, devices, or combinations of circuits and devices. In one embodiment, the regulated power supply comprises electrical contacts for coupling with a battery and one or more circuits for regulating the voltage and current delivered from the battery to the light source and the laser diode. The battery may be received within a compartment in a proximal end of the housing.

The regulated power supply operates the laser diode as close to 5 milliwatts (mw) as possible without exceeding 5 mw. Applicant has discovered that this power level provides effective treatment of oral ulcers and sores without damaging surrounding tissue.

The first and second switches activate the light source and the laser diode, respectively, and may be momentary push-button switches or any other types of switches. The switches are preferably located next to one another on the sidewall of the housing so that a user can quickly operate the switches with the same finger without re-gripping the device.

The control device may be a microprocessor, a microcontroller, an ASIC, or any other logic device or combinations of logic devices. The control device is configured to operate the laser diode for a selected time period each time the second switch is operated and to then subsequently turn the laser diode off until the switch is operated again. In one embodiment, the control device is pre-programed to operate the laser diode for approximately 30 seconds. The control device may also be field-programmable to permit selection of any laser diode operation time.

The housing encloses all of the other components of the device and is relatively small, lightweight, and handheld so that it can be easily held and manipulated by a dentist, doctor, consumer or other use. In one embodiment, the housing comprises a partially hollow tubular body approximately 10-18 cm long and approximately 1-3 cm in diameter.

In use, a dentist, doctor, consumer or other user may grip the device much like a pen and direct the distal end of the housing towards a patient's mouth without having to insert any part of the device into the oral cavity. The user may then activate the first switch to energize the light source to locate and illuminate an oral ulcer or sore to treat. Once an ulcer or sore is illuminated, the user may operate the second switch to energize the laser to treat the illuminated sore or ulcer. When the second switch is operated, the laser diode directs a collimated, coherent beam of radiation at the sore or ulcer for the selected time period (e.g. 30 seconds). After this time period has elapsed, the control device turns the laser diode off. The user may then operate the second switch a second time to continue treating the sore or ulcer for another selected time period.

The present invention provides numerous advantages over conventional laser therapy devices. For example, because all of the components of the device are enclosed in a portable, handheld housing, the device is easy to manipulate and use. Moreover, the device consistently and repeatedly delivers laser therapy at a selected wavelength and power and for a desired duration so that doctors, dentists, and other users can confidently use the device without safety and liability concerns.

This summary is provided to introduce a selection of concepts in a simplified form that are further described in the detailed description below. This summary is not intended to identify key features or essential features of the claimed subject matter, nor is it intended to be used to limit the scope of the claimed subject matter. Other aspects and advantages of the present invention will be apparent from the following detailed description of the embodiments and the accompanying drawing figures.

BRIEF DESCRIPTION OF THE DRAWING FIGURES

Embodiments of the present invention are described in detail below with reference to the attached drawing figures, wherein:

FIG. 1 is a perspective view of a laser treatment device constructed in accordance with embodiments of the present invention.

FIG. 2 is a side elevational view of the laser treatment device.

FIG. 3 is partial perspective view showing use of the device to treat an oral ulcer or sore of a patient.

FIG. 4 is a block diagram depicting certain components of the laser treatment device.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying drawings. The embodiments are intended to describe aspects of the invention in sufficient detail to enable those skilled in the art to practice the invention. Other embodiments can be utilized and changes can be made without departing from the scope of the claims. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

Turning now to the drawing figures, and particularly FIG. 1, a handheld laser device 10 constructed in accordance with embodiments of the invention is illustrated. As depicted in FIG. 3, the device 10 may be used by a dentist, doctor, nurse, consumer or other user to treat canker sores, cold sores, oral warts, fever blisters, acne and gingivitis, and other types of oral ulcers of sores 12, all of which are referred to herein as "oral ulcers or sores".

An embodiment of the device 10 is shown schematically in FIG. 4 and broadly comprises a light source 14; a laser diode 16; a regulated power supply 18; a first switch 20; a second switch 22; a control device 24; and a portable, handheld housing 26.

The light source 14 is positioned on a distal end of the housing and is provided for illuminating a patient's mouth so that a user may more easily locate an oral ulcer or sore to treat. The light source 14 may be any device that emits visible light such as a light emitting diode (LED) or incandescent lamp. In one embodiment, the light source 14 is a 3.5V light emitting diode (LED) that emits white light. As best shown in FIG. 1, the light source 14 may be positioned behind a water-resistant lens or glass cover to focus the light emitted therefrom and to resist migration of fluids into the device.

The laser diode 16 is also positioned on a distal end of the housing and is provided for emitting laser energy and directing it at a sore or ulcer to be treated. The laser diode 16 may be any device that emits electromagnetic radiation of wavelengths known to provide the desired bio-stimulatory effects. In one embodiment, the laser diode 16 is a 2V red laser diode that emits a spatially coherent, narrow beam of electromagnetic radiation having a wavelength of 600-700 nm, with a wavelength range of 630-680 nm being ideal. As with the light source 14, the laser diode 16 may be covered by a water-resistant lens or cover.

The regulated power supply 18 is provided for powering the light source 14 and laser diode 16 at selected power levels and may include any combination of power sources, voltage regulators, and/or current regulators. For example, one embodiment of the regulated power supply comprises electrical contacts 30 for coupling with a 1.5V AAA type battery 32 and one or more voltage/current regulating circuits 34,36 for regulating the voltage and current delivered from the battery 32 to the light source 14 and the laser diode 16.

In one embodiment, the regulated power supply 18 operates the laser diode 16 as close to 5 milliwatts (mw) as possible without exceeding 5 mw. Applicant has discovered that 5 mw is an optimum power level to effectively treat oral ulcers and sores without overheating and causing damage to surrounding tissue.

The first switch 20 is provided for selectively delivering power from the regulated power supply 18 to the light source 14. Likewise, the second switch 22 is provided to selectively deliver power to the laser diode 16. The first and second switches may be pushbutton switches or any other types of switches and are preferably located next to one another on the exterior wall of the housing near its distal end. The switches may also be combined into a single dual-switching device.

The control device 24 may be a microprocessor, a microcontroller, an ASIC, or any other logic device or combinations of logic devices. Control functions of the device, such as the treatment duration periods discussed herein, may be implemented with one or more computer programs stored in or on computer-readable medium residing on or accessible by the control device 24. Each computer program preferably comprises an ordered listing of executable instructions for implementing logical functions in the control device and can be embodied in any non-transitory computer-readable medium for use by or in connection with an instruction execution system, apparatus, or device. In the context of this application, a "computer-readable medium" can be any non-transitory means that can store the program for use by or in connection with the instruction execution system, apparatus, or device.

The control device 24 is programmed or otherwise configured to operate the laser diode 16 for a selected time period each time the second switch 22 is operated and to then subsequently turn the laser diode off until the switch is operated again. In one embodiment, the control device 24 is pre-programed to operate the laser diode for approximately 30 seconds, but it may also be field-programmable to permit selection of any laser diode operation time. The control device may also be programmed to operate the light source 14 for a pre-determined amount of time each time the first switch 20 is operated so that it can continue to illuminate a patient's mouth after the first switch is released.

In an alternative embodiment, the first and second switches 20,22 include, or are coupled with, timers that operate the light source 14 and laser diode 16 for pre-determined time intervals without the need for a separate control device. For example, the first and second switches 20,22 may be operable to operate the light source 14 and laser diode 16 for 45 seconds and 30 seconds, respectively, each time the switches are activated.

The housing 26 encloses all of the other components of the device 10 in a relatively small, lightweight, and handheld package that can be easily held and manipulated by a dentist, physician, consumer, or other use. The housing 26 may be constructed of any suitable lightweight material such as thin gauge aluminum, stainless steel or other metal, and comprises a hollow tubular body approximately 10-18 cm long and approximately 1-3 cm in diameter. In one particular embodiment, the housing is approximately 14 cm long and 2 cm in diameter. The proximal end of the housing may include a screw-off cap 38 that exposes a hollow compartment that holds the battery 32. The housing may include appropriate seals so that it is substantially water-proof.

The housing 26 may also include a grip pad 40 that partially encircles the portion of the housing near the switches 20,22 to assist a user in more firmly and comfortably gripping the device 10.

In use, a dentist, physician, consumer, or other user may grip the device 10 much like a pen and direct the distal end of the housing toward the patient's mouth. The user may then activate the first switch 20 to energize the light source 14 to locate and illuminate an oral ulcer or sore to treat. Once an ulcer or sore is illuminated, the user may operate the second switch 22 to energize the laser 16 to treat the illuminated sore or ulcer. When the second switch 22 is operated, the laser diode 16 directs a collimated, coherent beam of radiation at the sore or ulcer for the selected time period (e.g. 30 seconds). After this time period has elapsed, the control device 24 turns the laser diode off, and the user may operate the second switch a second time to continue treating the sore or ulcer.

The present invention provides numerous advantages over conventional laser therapy devices. For example, because all of the components of the device are enclosed in a portable, handheld housing, the device is easy to manipulate and use. Moreover, by providing the device with a regulated power supply and control device, the device consistently and repeatedly delivers laser therapy at a selected wavelength and power and for a desired duration so that physicians, dentists, consumers and other users can confidently use the device without safety and liability concerns.

Although the invention has been described with reference to the preferred embodiment illustrated in the attached drawing figures, it is noted that equivalents may be employed and substitutions made herein without departing from the scope of the invention as recited in the claims.

Having thus described the preferred embodiment of the invention, what is claimed as new and desired to be protected by Letters Patent includes the following:

1. A handheld device for treating an oral ulcer or sore, the device comprising:
   a light emitting diode (LED) for emitting a white beam of light;
   a first pushbutton switch;
   a laser diode for emitting a collimated coherent beam of laser energy of a wavelength of between 600-700 nm;
   a regulated power supply for powering the laser diode at between 4 and 5 mw for treating the oral ulcer or sore at a power of as close to 5 mw as possible without exceeding 5 mw;
   a second pushbutton switch operable to selectively deliver power from the regulated power supply to the laser diode when the second pushbutton switch is operated by a user to treat the ulcer or sore;
   a control device configured to operate the laser diode for a pre-programmed duration of 5, 10, or 30 seconds each time the second pushbutton switch is operated and to subsequently turn the laser diode off until the second pushbutton switch is operated again, the first pushbutton switch being operable to selectively deliver power from the regulated power supply to the LED to locate and illuminate the oral ulcer or sore while the laser energy is directed at the oral ulcer or sore and to continue to illuminate the oral ulcer or sore for a pre-programmed amount of time after the laser diode is turned off; and
   a portable, handheld housing comprising a hollow tubular body between 10-18 cm long and between 1-3 cm in diameter for housing the laser diode, the regulated power supply, the first and the second pushbutton switches, the light emitting diode, and the control device, the second pushbutton switch being located near the first pushbutton switch on a sidewall of the housing so that the user can quickly operate the pushbutton switches with the same finger without re-gripping the handheld device.

2. A handheld device for treating an oral ulcer or sore, the device comprising:
   a laser diode for emitting a collimated coherent beam of laser energy of a wavelength of between 600-700 nm;
   a regulated power supply for powering the laser diode at between 4 and 5 mw for treating the oral ulcer or sore at a power of as close to 5 mw as possible without exceeding 5 mw;
   a light emitting diode (LED) for emitting a white beam of light;
   a single dual-switching pushbutton switch operable to selectively deliver power from the regulated power supply to the LED to locate and illuminate the oral ulcer or sore while the laser energy is directed at the oral ulcer or sore and to continue to illuminate the oral ulcer or sore for a predetermined amount of time after the laser diode is turned off, and to selectively deliver power from the regulated power supply to the laser diode when the dual-switching pushbutton switch is operated by a user to treat the ulcer or sore;

a control device configured to operate the LED and the laser diode for a pre-programmed duration of 45 seconds or less each time the dual-switching pushbutton switch is operated and to subsequently turn the LED and the laser diode off until the dual-switching pushbutton switch is operated again, the dual-switching pushbutton and the control device being cooperatively configured such that the dual-switching pushbutton switch does not terminate power to the LED and the laser diode when the LED and the laser diode are on and the dual-switching pushbutton switch is operated; and a portable, handheld housing comprising a hollow tubular body between 10-18 cm long and between 1-3 cm in diameter for housing the laser diode, the regulated power supply, the dual-switching pushbutton switch, the light emitting diode, and the control device.

* * * * *